United States Patent
Eriksson

(10) Patent No.: US 10,384,080 B2
(45) Date of Patent: Aug. 20, 2019

(54) INCREMENTAL TREATMENT PLANNING

(71) Applicant: RaySearch Laboratories AB, Stockholm (SE)

(72) Inventor: Kjell Eriksson, Stockholm (SE)

(73) Assignee: RaySearch Laboratories AB, Stockholm (SE)

( * ) Notice: Subject to any disclaimer, the term of this patent is extended or adjusted under 35 U.S.C. 154(b) by 490 days.

(21) Appl. No.: 15/106,097

(22) PCT Filed: Dec. 20, 2013

(86) PCT No.: PCT/EP2013/077755
§ 371 (c)(1),
(2) Date: Jun. 17, 2016

(87) PCT Pub. No.: WO2015/090459
PCT Pub. Date: Jun. 25, 2015

(65) Prior Publication Data
US 2016/0303398 A1     Oct. 20, 2016

(51) Int. Cl.
*A61N 5/10* (2006.01)

(52) U.S. Cl.
CPC .... *A61N 5/1031* (2013.01); *A61N 2005/1035* (2013.01)

(58) Field of Classification Search
CPC .... A61N 5/103; A61N 5/1031; A61N 5/1038; A61N 5/1039; A61N 2005/1041
USPC .......................................................... 600/1–8
See application file for complete search history.

(56) References Cited

U.S. PATENT DOCUMENTS

| | | | |
|---|---|---|---|
| 5,373,844 A | 12/1994 | Smith et al. | |
| 2003/0212325 A1 | 11/2003 | Cotrutz et al. | |
| 2007/0201614 A1* | 8/2007 | Goldman | A61N 5/1031 378/65 |
| 2008/0008291 A1* | 1/2008 | Alakuijala | A61N 5/103 378/65 |
| 2009/0326615 A1* | 12/2009 | Nord | A61N 5/103 607/88 |

FOREIGN PATENT DOCUMENTS

| EP | 2 260 902 A1 | 12/2010 |
|---|---|---|
| WO | WO-2005/035061 A2 | 4/2005 |
| WO | WO-2013/049845 A2 | 4/2013 |

OTHER PUBLICATIONS

International Search Report in International Application No. PCT/EP2013/077755 dated Sep. 15, 2014.

\* cited by examiner

*Primary Examiner* — Samuel G Gilbert
(74) *Attorney, Agent, or Firm* — Drinker Biddle & Reath LLP

(57) ABSTRACT

A method for generating a radiotherapy treatment plan for a patient is provided. The treatment plan is optimized using an optimization objective which is at least partly based on an initially planned dose to the patient.

16 Claims, 3 Drawing Sheets

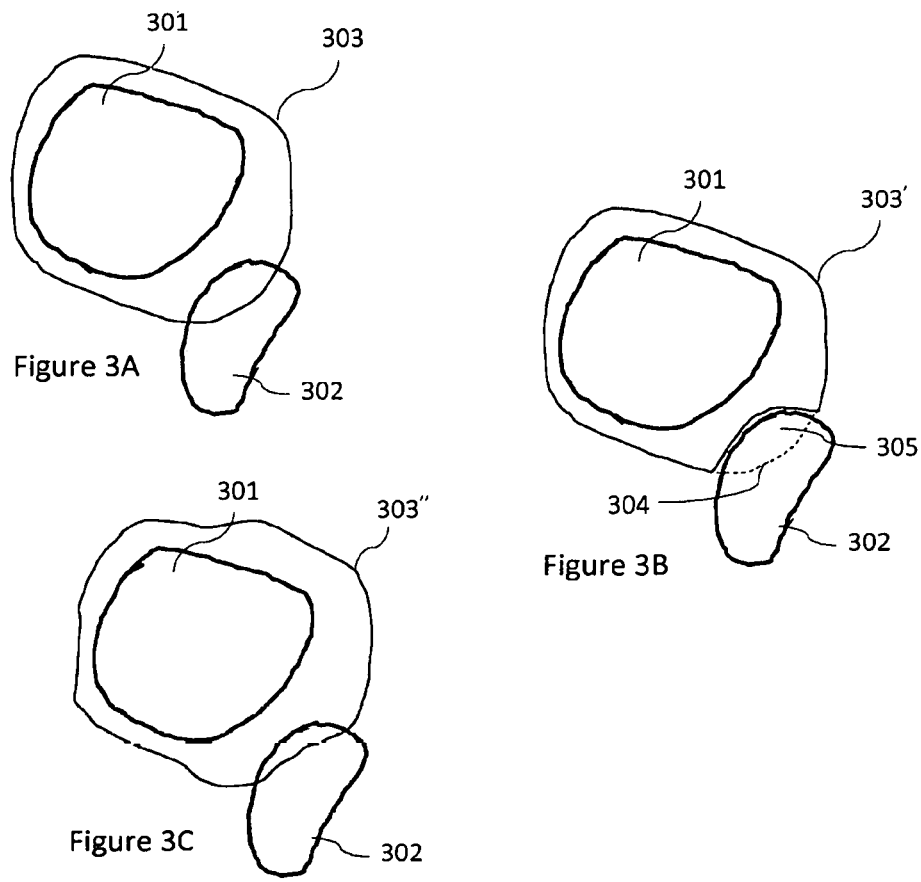
Figure 3A
Figure 3B
Figure 3C
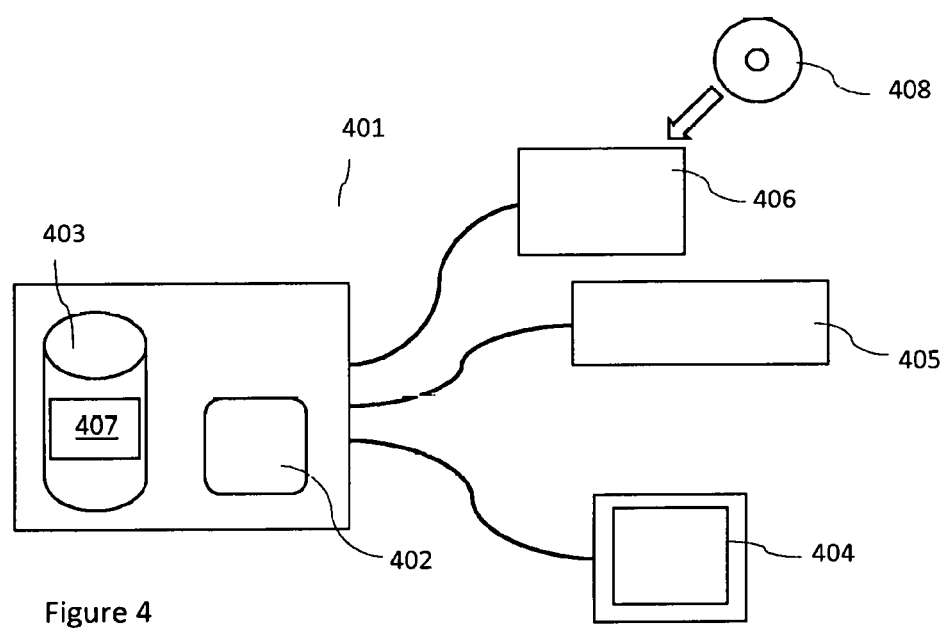
Figure 4

INCREMENTAL TREATMENT PLANNING

CROSS REFERENCE TO RELATED APPLICATIONS

This application is a § 371 National Stage Application of PCT International Application No. PCT/EP2013/077755 filed Dec. 20, 2013, the entire contents of which is incorporated by reference herein in its entirety.

FIELD OF THE INVENTION

The present invention relates to radiotherapy treatment planning, and in particular to optimization of radiotherapy treatment plans.

BACKGROUND

In radiotherapy, the goal is typically to deliver a sufficiently high radiation dose to a target (for example a tumor) within the patient, while sparing surrounding normal tissue as far as possible. In particular, it is important to minimize the dose to sensitive organs close to the target. A treatment plan, defining treatment parameters, such as treatment machine settings, to be used in a radiotherapy treatment session, is usually determined with the aid of a computer-based treatment planning system. In inverse treatment planning, an optimization algorithm is employed for finding a set of treatment parameters that will generate an acceptable dose distribution within the subject, preferably satisfying all the clinical goals defined by the clinician. However, the treatment plan optimization process does not in any way guarantee that the best possible treatment plan is obtained. The result is in general depending on the experience of the treatment planner and, for example, the selection of treatment objectives used for the optimization. A substantial amount of "trial-and-error" is usually required, even for an experienced treatment planner, before an acceptable treatment plan has been found.

Furthermore, if a dose distribution of an optimized treatment plan is satisfactory in most regards but comprises some small deficiency, it might not be apparent to a treatment planner how to adjust the optimization objectives or constraints (or the objective weights) in order to remedy the deficiency.

An aim of the present invention is to overcome, or at least mitigate, the drawbacks described above, and in particular to provide a treatment planning system that will enable a treatment plan to be generated that satisfies clinical goals to a greater extent.

SUMMARY

According to one aspect of the invention, a method for generating a radiotherapy treatment plan for a patient is provided. Preferably, the method comprises, in a processor: optimizing treatment parameters on the basis of one or more optimization objectives, wherein one or more of the optimization objectives is at least partly based on an initially planned dose comprised in an initial radiotherapy treatment planning result for the patient and obtained prior to generating the radiotherapy treatment plan.

According to another aspect of the invention, a computer program product is provided. Preferably, the computer program product comprises computer-readable instructions which, when executed on a computer, will cause the computer to perform the method for generating the radiotherapy treatment plan.

According to yet another aspect of the invention, a computer system is provided. Preferably, the computer system comprises a processor coupled to at least one memory having stored thereon a computer program comprising computer-readable instructions for generating the radiotherapy treatment plan, wherein the processor is configured to execute the computer-readable instructions.

The present invention is based on the recognition that treatment plan optimization is more effective when being based on treatment goals which are close to being achievable. Hence, the present invention proposes an optimization process for obtaining an optimal treatment plan, where the optimization is partly based on a dose distribution resulting from initial treatment planning. When generating the treatment plan by using an optimization objective based on an initially planned dose, the optimization objective will reflect a dose which is achievable, or at least close to being achievable. Therefore, the treatment planning will be effective and there will be a good chance of obtaining a satisfactory treatment plan. The initial radiotherapy treatment planning result can be the result of any conventionally used treatment planning method and could for example be based on inverse treatment planning where an optimization algorithm is employed for finding a set of treatment parameters that will generate a dose which, as far as possible, satisfies specified treatment goals.

According to some embodiments, the initial treatment planning result comprises initially planned treatment parameter settings which are utilized when generating the radiotherapy treatment plan. Hence, a "warm start" is obtained where initially planned variable settings are used as starting point for the treatment plan optimization. This could result in reduced computational time and is particularly useful when only introducing minor modifications to the optimization objectives.

According to some embodiments, one or more of the optimization objectives is at least partly based on the spatial dose distribution corresponding to the initially planned dose. Hence, the treatment planning will aim at preserving the actual spatial distribution of the dose achieved in initial treatment planning.

According to some embodiments, one or more of the optimization objectives is at least partly based on a dose volume histogram corresponding to the initially planned dose. Thereby, the treatment planning would aim at preserving the dose-volume statistics rather than the spatial characteristics of the initially planned dose According to some embodiments, one or more of the optimization objectives is at least partly based on a characteristic dose fall-off corresponding to the initially planned dose. Hence, a characteristic dose fall-off, describing how the initially planned dose depends on the distance to the target, is preserved.

According to some embodiments, one or more of the optimization objectives is an additional objective not based on said initially planned dose. Hence, an additional treatment objective is used in combination with an objective based on the initially planned dose. The additional objective might be used to specifically address some aspect of the initially planned dose which needs to be improved. On the other hand, the objective based on the initially planned dose will repress any unwarranted, substantial changes of the initially planned dose distribution.

According to some embodiments, one or more of said optimization objectives is at least partly based on a modification of said initially planned dose. Hence, a partly modified initially planned dose is used as basis for at least one optimization objective. The modification of the dose could specifically address some aspect of the initially planned dose which needs to be improved. Since also parts of the dose distribution which have not been modified are used as basis for the optimization objective, any unwarranted, substantial changes of the unmodified initially planned dose distribution will be repressed.

According to some embodiments, user-input regarding an additional objective and/or a modification of said initially planned dose is received from a user via a user-input interface and utilized for defining one or more of said optimization objectives. Thereby, user-input, which could be based on an evaluation of the initial treatment planning result, can be incorporated into the treatment planning process. Advantageously, such user-input can be continuously received during the optimization process, allowing a user to efficiently control the treatment planning result.

BRIEF DESCRIPTION OF THE DRAWINGS

FIG. 3A schematically illustrates a target region, an organ at risk region, and a dose distribution resulting from initial treatment planning. FIG. 3B schematically illustrates a modified dose distribution used as objective for incremental treatment planning. FIG. 3C schematically illustrates a resulting dose distribution after incremental treatment planning.

FIG. 4 is a schematic illustration of a computer system according to an example embodiment of the invention.

DETAILED DESCRIPTION

Treatment planning is usually performed on the basis of internal images of the patient, such as computed tomography (CT) scans, and on internal structures defined and segmented in these images. FIGS. 3A-3C are schematic illustrations of a two-dimensional representation of a patient, e.g. corresponding to one slice of CT scan. The three-dimensional representation of the patient is often discretized into a plurality of voxels for the purpose of dose calculation and treatment planning.

Figure 1:
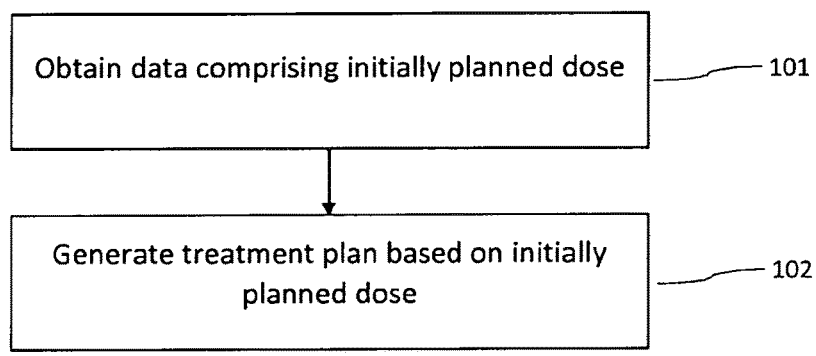
FIG. 1 is a flowchart of a method according to the invention.

FIG. 1 is a flowchart of a method according to an embodiment of the invention. In step 101, data relating to an initial treatment planning result is obtained. The initial treatment planning result comprises at least an initially planned dose. Initial treatment planning could involve conventional forward treatment planning where a treatment planner defines treatment parameter settings, for example based on experience, and the resulting dose is calculated. The treatment planner can modify parameters and repeat the dose calculation until he or she is satisfied with the result. However, the initial treatment planning would in general involve inverse treatment planning, where an optimization algorithm is employed for finding a set of treatment parameters that will generate a dose which, as far as possible, satisfies all the various objectives and/or constraints defined by the treatment planner (where these objectives in turn are defined on the basis of the clinical goals for the treatment, for example as defined by a radiation oncologist). Hence, the initial treatment planning could correspond to any kind of treatment planning process for determining a radiotherapy treatment plan. For example, a conventional inverse treatment planning method could be used or more recent techniques, such as Multi-Criteria Optimization, could be used. A treatment plan can be optimized for use in any kind of radiation treatment apparatus using any kind of modality including photons, protons or electrons. The treatment plan can be an Intensity Modulated Radiation Therapy (IMRT) plan or any other radiation treatment plan, such as, for example, a Three-Dimensional Conformal Radiation Therapy (3DCRT) plan or a Volumetric Modulated Arc Therapy (VMAT) plan.

When optimizing a treatment plan, each optimization objective might be represented by a corresponding optimization function. A common approach in inverse treatment planning, which for example could be employed for the initial treatment planning, is to minimize (or maximize) an objective function composed of all optimization functions, often subject to certain planning constraints. The objective function $f$ can be a weighted sum of the optimization functions $f_i$, i.e., $$f = \sum_i w_i f_i \qquad (1)$$

where the weights $w_i$ of the optimization functions correspond to the rates at which a decrease in one optimization function value is traded for an increase in a second optimization function value, relating to another, possibly conflicting, treatment goal. The weights are specific for the different optimization functions. It is possible to also use voxel-specific weights in the optimization functions, reflecting the relative importance of satisfying the objectives in different voxels.

A simple example of an optimization function $f_i$ corresponding to a uniform dose optimization objective defined for a specific region of interest (ROI), such as a target volume or an organ at risk (OAR), comprising j voxels is:

$$f_i = \sum_j \Delta v_j \left( \frac{d_j - d^{ref}}{d^{ref}} \right)^2 \qquad (2)$$

where $d_j$ is the dose in voxel j, $d^{ref}$ is the reference dose, and $\Delta v_j$ is the relative volume of voxel j in the ROI. The dose $d_j$ is a function of the treatment parameters which are to be determined by the optimization, and the reference dose $d^{ref}$ is the dose objective relating to a desired dose in the ROI. The normalization by multiplying with the relative volume $\Delta v_j$ and dividing by the square of the reference dose $d^{ref}$ has the effect that, disregarding objective weights, all ROIs are considered to be equally important irrespective of volume and reference dose level. Using a-uniform dose optimization function as defined in (2), both under- and overdosage with respect to the reference dose level are equally penalized. This is only one example, and, as would be apparent to a person skilled in the art, many other optimization objectives and corresponding optimization functions can be employed instead of or in addition to, this function. Examples of such are minimum or maximum dose optimization functions, minimum or maximum dose volume histogram (DVH) based optimization functions, or radiobiologically based optimization functions.

Various different optimization techniques may be employed when optimizing an objective function to arrive at a treatment plan. For example, gradient-based methods, such as methods based on sequential quadratic programming algorithms, or heuristic methods, such as simulated annealing, can be used. The optimization might be fluence-based, which requires subsequent conversion to machine parameters, or based on Direct Machine Parameter Optimization (DMPO) where machine parameters are directly optimized, or a combination of both. Conventional inverse treatment planning using optimization is well-known in the art and will therefore not be described in further detail herein.

The result of the initial treatment planning will be an initially planned dose and a set of initially planned treatment parameters. According to the invention, though, this treatment plan is not used as a final treatment plan.

In step 102, a treatment plan is generated at least partly based on the initially planned dose. The treatment planning in step 102 is herein referred to as "incremental" treatment planning or optimization, indicating that this treatment planning is based on the initially planned dose distribution. The initially planned treatment parameters resulting from the initial treatment planning might also be utilized in the incremental treatment planning in order to improve the efficiency of the overall treatment planning process.

The incremental optimization employs optimization of an objective function which includes one or more optimization objectives at least partly based on the dose distribution determined in the initial treatment planning. Preferably, an additional optimization objective not based on the initially planned dose, or some minor modification of the initially planned dose, is also incorporated in the optimization. However, at least some of the initially used optimization objectives are disregarded in the incremental optimization. According to some example embodiments, all of the previously used objectives are disregarded. According to alternative example embodiments, one or more of the initially used optimization objectives are kept for the incremental treatment planning and used in combination with the optimization objectives based on the initially planned dose. Preferably, the one or more optimization objectives which are kept relates to clinical goals which have not been fulfilled in the initial treatment planning.

Hence, an optimization which, at least in part, aims at obtaining a specific dose distribution (i.e. the dose distribution obtained from initial treatment planning) is performed. Such optimization is herein referred to as "dose mimicking", indicating that the goal of the optimization is to find a set of treatment parameters which produces a dose distribution which as closely as possible matches or "mimics" a specific dose distribution. Dose mimicking could be based on the spatial dose distribution, i.e. using reference dose objectives which are different and specific for each voxel. Alternatively or additionally, dose mimicking could be based on dose volume histograms (DVHs), i.e. using the previously obtained DVH curves as references in the optimization. Alternatively or additionally, a reference dose fall-off function can be determined from the initially planned dose and used as optimization objective. These different dose mimicking methods are described in further detail below:

Spatial Dose Mimicking

When mimicking the spatial dose distribution, optimization functions similar to the function as defined in equation (2) in the example above could be used, with the difference that the reference dose is specific for each voxel. That is, within the context of the present invention, the reference dose of a voxel corresponds to the initially planned dose to the voxel. Hence, the differential $(d_j - d_j^{ref})$ is used in the optimization functions where $d_j^{ref}$ is the reference dose specific for voxel j. Different dose mimicking optimization functions could be used in different regions. For example, an optimization function penalizing both under- and overdosage in a voxel (e.g. similar to a function according to equation 2, but using voxel-specific reference dose levels) could be used for targets, while an optimization function penalizing only overdosage could be used in other regions, such as in regions corresponding to specified organs at risk (OARs).

DVH Mimicking

When mimicking a DVH curve, various methods could be employed. As an example, a uniform reference DVH optimization function could be used. In relation to a maximum- or minimum DVH optimization function, which only penalizes deviations with respect to a specific point on a DVH curve, a uniform reference DVH optimization function penalizes any discrepancy between the DVH curve of the plan to be optimized and the reference DVH curve. For example, if defining a function D(v) parameterizing the DVH curve as a function of cumulative volume (letting D(v) be the smallest dose level d such that the volume fraction v receives a dose greater than d), an optimization function $f$ could take the form $$f = \int_0^1 (D(v) - D^{ref}(v))^2 dv \qquad (3)$$

where D(v) refers to the DVH of the plan to be optimized and $D^{ref}(v)$ refers to the reference DVH curve (e.g. the DVH curve being the result of the initial treatment planning). Normalization using some kind of reference dose level, e.g. corresponding to a normalization according to equation (2), could preferably also be incorporated in the optimization function.

DVH curves do not comprise any spatial information but are simple 2D representations of the dose distribution in specific structures. Hence, when using DVH-based dose mimicking, the optimization would focus more on the dose-volume statistics and less on the spatial characteristics of the dose distribution.

Dose Fall-Off Mimicking

A reference dose fall-off mimicking serves to replicate dose fall-off outside a target volume of a reference dose distribution. Hence, for each voxel j in a region where dose fall-off is to be mimicked, an approximate shortest distance $\delta_j$ to the target volume is computed. A dose fall-off function $\Delta(\delta)$ that approximately describes how the reference dose, i.e. the initially planned dose, depends on the distance to the target is then constructed. The optimization function is finally defined, for example analogously with an optimization function similar to equation (2), but with the dose fall-off function substituted for the reference dose level, i.e. such that the differential $(d_j - \Delta(\delta_j))$ is used in the optimization function.

Using this approach, the reference dose for a voxel will not completely correspond to the initially planned dose to the voxel (as for dose distribution mimicking), but rather being calculated in accordance with a characteristic dose fall-off determined from the initially planned dose distribution. As a simple example, the fall-off function $\Delta(\delta_j)$ could be constructed so that the reference dose for a voxel j at a distance $\delta_j$ from the target is an average dose, according to the initially planned dose distribution, for all voxels at a corresponding distance from the target.

Any of the described dose mimicking optimization functions could be combined with each other and/or with other optimization functions in the objective function, as will be discussed below with reference to FIG. 2B.

Dose mimicking optimization functions might not only be used in the incremental treatment planning but also when determining the initially planned dose. As one example, a desired dose distribution could be defined by a user and employed as optimization objective in the initial treatment planning. Hence, a user could "paint", or in any other way, using any suitable user interface, define a desired dose distribution within the patient. Alternatively or additionally, a reference dose fall-off function, as described above, could be employed, advantageously in combination with some specified desired dose levels in various regions, for defining the desired dose distribution. The desired dose distribution is thereafter used as optimization objective in a dose mimicking optimization in accordance with description above. The planned dose resulting from the dose mimicking optimization will usually not correspond completely to the desired dose distribution since the desired dose might not be achievable. Nonetheless, the planned dose distribution is used as basis for the subsequent incremental treatment planning, disregarding the desired dose distribution previously used as optimization objective. Thereby, the incremental treatment planning will be based on an actually obtainable dose distribution, and not merely on a desired dose distribution.

Figure 2A:
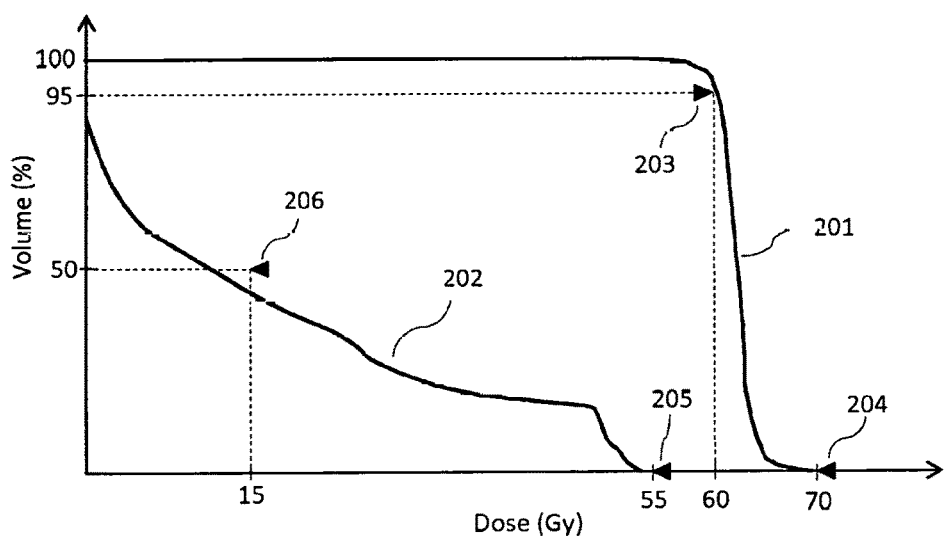
FIG. 2A illustrates dose volume histograms of a target and an organ at risk resulting from initial treatment planning.

FIG. 2A illustrates dose volume histogram (DVH) curves indicating the result of an initial treatment planning. Accordingly, a target region DVH curve 201, and a risk organ DVH curve 202, show the dose delivered to these structures in accordance with the initial treatment planning. Although only two DVH curves are shown, it is to be understood that many DVH curves relating to various different structures could result from the initial treatment planning and be used as basis for an optimization objective utilized in the incremental treatment planning step. The initial treatment planning could be an inverse treatment planning process utilizing optimization of a number of objectives. In this example embodiment, the objectives 203, 204, 205, 206 are indicated in FIG. 2A as small arrows in the DVH graph. A minimum DVH objective 203 was assigned to the target volume defining that at least 95% of the volume should receive 60 Gy or more. A maximum dose objective was also assigned to the target, defining that no part of the target should receive more than 70 Gy. Another maximum dose objective 205, assigned to the risk organ, defined that no part of the organ should receive more than 55 Gy. Finally, a maximum DVH objective, defining that at most 50% of the organ may receive more than 15 Gy was assigned to the risk organ. These are only examples of optimization objectives which could be used for the initial treatment planning step. Many alternative objectives and/or constraints could be employed instead of, or in addition to, these, corresponding to both physical (i.e. entirely dose based) and biologically based optimization functions.

Figure 2B:
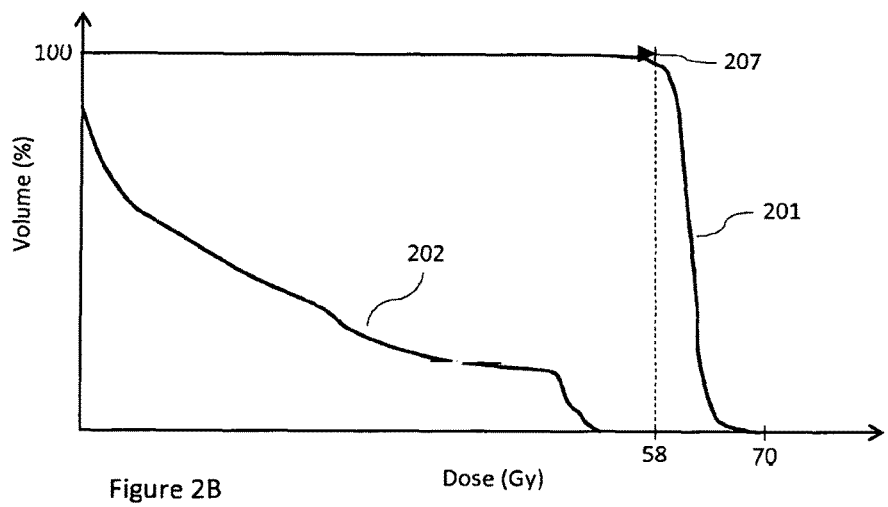
FIG. 2B illustrates the objectives used for incremental treatment planning.

FIG. 2B illustrates the optimization objectives used in the subsequent incremental treatment planning step. The DVH curves 201, 202 being the result from the initial optimization is now used as objectives together with one additional objective 207 defining a minimum dose of 58 Gy to the target. The previously used objectives are disregarded altogether in the incremental optimization step. Further, or other, additional objectives and corresponding optimization functions could be incorporated in the objective function in the incremental optimization. For example, objectives relating to dose uniformity, average dose, equivalent uniform dose (EUD), tumor control probability (TCP), normal tissue complication probability (NTCP), or any other physical or biologically based optimization function, could be used. However, the objective function employed in the incremental optimization step will always be at least partly based on the initially planned dose resulting from the initial treatment planning, preferably by dose mimicking optimization functions, as discussed above. In FIG. 2B, the initially planned dose which is used as optimization objective in the incremental planning is illustrated by DVH curves 201, 202. An exemplary objective function to be used in the incremental optimization could therefore be composed of two DVH mimicking optimization functions (one for each DVH), and one minimum dose optimization function. However, it is possible to use spatial dose distribution mimicking functions and/or reference dose fall-off functions, in combination with, or instead of, DVH mimicking functions. These dose mimicking optimization functions could in a corresponding way be combined with additional objectives such as the minimum dose objective 207.

Figure 2C:
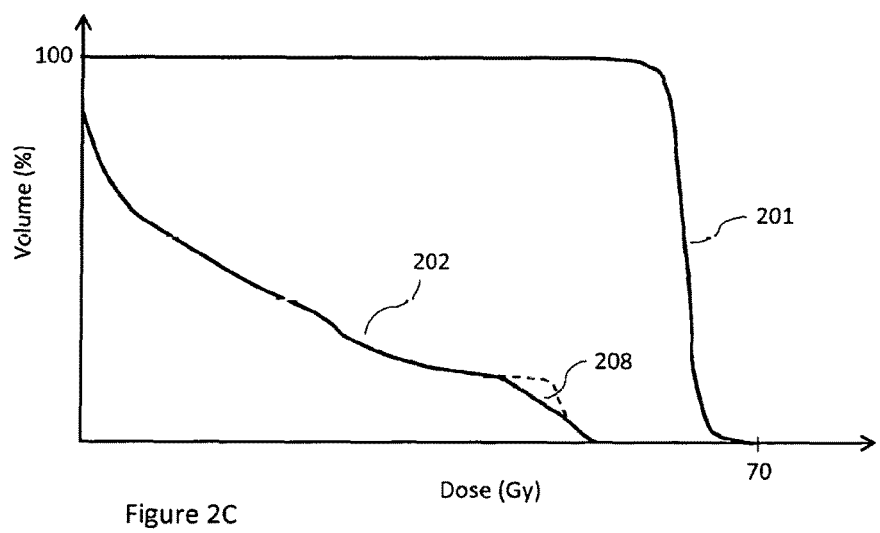
FIG. 2C illustrates an alternative of objectives used for the incremental treatment planning.

FIG. 2C illustrates an alternative optimization objective used in the incremental treatment planning. As can be seen in the figure, a modified DVH curve 202', comprising a minor modification 208, is now used as objective together with the unmodified DVH curve 201. The incremental optimization using the DVH curves 202' and 201 as objectives is performed by DVH mimicking optimization, as described above.

A minor modification of a DVH curve, which is used as input to the incremental optimization algorithm, could relate to a specific dose discrepancy that the treatment planner wants to remedy. In the example shown in FIG. 2C, the modification 207 aims at reducing a dose anomaly in the OAR DVH, seen as a "bump" in the otherwise relatively smooth DVH, which could be indicative of a so called "hot spot" (a part of the region receiving unreasonably high dose). Any kind of user interface could be used allowing a treatment planner to input the desired modification of the initially planned dose. As one example, a user interface could allow a user to click, for example using a mouse, on a DVH curve and "drag" some part of the curve a desired distance in a desired direction. This would result in a slightly modified DVH curve which, together with the unmodified DVH curves relating to the other structures, would constitute the optimization objectives of the incremental optimization, as described above.

In other embodiments involving interactive manipulation of dose distributions for modifying optimization objectives, the complete three-dimensional dose distribution resulting from the initial optimization could be used as basis for the incremental optimization, i.e. using spatial dose mimicking. Such an embodiment is first described with reference to FIGS. 3A-3C. FIG. 3A shows a cross section of the patient (e.g. corresponding to a CT slice) comprising a target region 301 and an organ at risk (OAR) region 302 and a dose distribution resulting from an initial treatment planning step, illustrated by an isodose contour 303 corresponding to some specific dose level.

According to this example embodiment, a minor modification of the dose distribution is defined directly in the image, using any suitable user interface. For example, a hot or a cold spot could be addressed by interactively dragging a part of the relevant isodose contour a desired distance in a desired direction. In FIG. 3B, a part of the isodose contour (illustrated by the dashed line) has been moved towards the target so that the isodose does not cover the OAR 302, resulting in a modified isodose contour 303'. This creates a modified dose distribution used as objective for the incremental optimization, where the modified dose distribution corresponds to the previously obtained dose distribution except in voxels within, and possibly in the vicinity of a region 305. The region 305 corresponds to the modified isodose contour 303' subtracted from the previous isodose contour 303. An isodose contour modification can be translated to modified dose objectives in the related voxels in various ways. For example, each voxel within the region 305 might be assigned a dose objective a predefined level below the dose level corresponding to isodose 303. As another alternative, the dose objective of a voxel within region 305 could be based on an interpolation of the dose according to the isodose contour 303 and the dose according to an isodose of some specified lower dose level, i.e. corresponding to a specific isodose contour (not illustrated) located further outside isodose contour 303. The modified reference dose level of a voxel within region 305 would thus depend on the relative location of the voxel in view of the modified isodose contour 303' and an isodose contour corresponding to a specified lower dose level in the initially planned dose distribution. The importance weights used in the optimization might be adjusted, e.g. increased according to some predetermined criteria, for voxels having modified reference dose levels (e.g. voxels within the region 305). Thereby, the incremental optimization would prioritize obtaining the proposed dose modifications over preserving the dose levels in voxels having unmodified reference dose.

A dose mimicking optimization used in the incremental treatment planning step would then try to obtain the modified dose distribution having a modified isodose contour 303'. FIG. 3C shows a dose distribution comprising an updated isodose contour 303" resulting from the incremental treatment planning step, which for example could comprise spatial dose mimicking optimization as described above. As seen in the figure, the dose modification from FIG. 3B has been partly satisfied, while the dose is only slightly changed in adjacent regions. If the treatment planner is satisfied with the result, the treatment plan is approved and used for treating the patient. If not satisfied, the treatment planner might try some other modification of the dose distribution, or add some other additional optimization objective. In FIGS. 3A-3C, the dose distribution is displayed and modified in a two-dimensional view (e.g. corresponding to a CT slice of the patient). Alternatively or additionally, the dose distribution can be visualized and modified directly in a 3D view of the patient.

As an alternative to modifying isodose contours, a user interface allowing "drawing" a desired dose modification, such as a modified dose distribution according to FIG. 3B, might be used. For example, a "brush" tool, similar to tools sometimes used for modifying structure contours in an image segmentation process, could be used. Thereby, using the tool, a desired adjustment of a dose might be directly specified in the image, for example by positioning and/or clicking a mouse pointer, or using any other data input device, in regions within the image where the dose distribution is to be adjusted. The extension of the brush tool could be defined by the user. Accordingly, when using the tool, the dose levels might be adjusted for all voxels covered by the brush. For example, a "reduce dose" and/or "increase dose" functionality might be used for reducing or increasing, respectively, the dose in a region (e.g. one or more voxels) regardless of the previous dose level in the region. The dose adjustments could differ for different voxels depending on the relative position within the region covered by the brush. For example, the voxel in the center of the region covered by the brush might be adjusted more than peripheral voxels in said region. User commands for increasing dose and/or reducing dose could be input using any suitable data input device, such as, for example, a mouse button and/or a mouse wheel etc. The brush tool might be used as a 2D tool, e.g. only modifying voxels in the presently displayed CT slice. Alternatively, the brush tool might be used as a 3D tool employed within a 2D- or a 3D patient view, modifying all voxels within a volume covered by the brush tool (e.g. a volume defined by a sphere-shaped brush having a user-defined radius).

In embodiments relating to interactive treatment planning as described above, it is preferable that the incremental optimization is continuously running, i.e. the optimization is not terminated or paused or otherwise ended before the system receives a user command instructing the optimization to stop. Thus, the optimization do not automatically stop after a certain number of iterations, or when a specific objective function value has been obtained or similarly, which would usually be the case in a conventional treatment plan optimization process. Instead, the optimization continue until the user is satisfied with the dose distribution or for other reasons wants to stop the optimization. Hence, the system will continuously try to obtain the dose distribution defined by the initially planned dose and the modifications of this dose as input by the user.

There are no guarantees that the incremental optimization will be able to, in an acceptable way, fulfil the desired modifications of the dose distribution. However, if the optimization and dose calculation algorithms are sufficiently fast, interactive treatment planning with near real-time feedback will be provided. Thus, the user would interactively modify the initially planned dose distribution, using any suitable tool, and almost immediately see the resulting dose distribution after optimization. Hence, a user could indicate small modifications of the optimization objective (i.e. the initially planned dose distribution) while the dose mimicking optimization algorithm is running, and immediately receive an indication regarding whether the modifications were achievable or whether the cost, in view of modified dose to other structures and/or impaired fulfillment of other treatment goals, was too high. Accordingly, the treatment planner can efficiently try out various modifications of the optimization objectives until he or she finds a resulting dose distribution to his or her liking. This is facilitated since the optimization objectives are partly based on an actually achieved dose distribution and therefore are always close to being achievable (provided that the proposed modifications are small).

According to some embodiments, a user can "reset" the dose used as basis for the incremental treatment planning. Hence, the user could at any time select to replace the initially planned dose with the current dose (for example obtained during interactive incremental treatment planning as described above) such that the current dose will be considered as an initially planned dose in any subsequent optimization. In other words, the result of incremental treatment planning can be selected to represent an initial treatment planning result used as basis for further incremental treatment planning.

Although incremental optimization could start from scratch, i.e. not utilizing the initially planned treatment parameters but only the initially planned dose as basis for new optimization objectives, it might sometimes be advantageous to also utilize some or all of the treatment parameter settings resulting from the initial treatment planning. These parameter settings could be used as starting points in the incremental optimization. Generally, as long as only minor modifications are made, such optimization would allow for a reduction in computational time.

FIG. 4 schematically illustrates an example of a computer system 401 according to the invention. The system comprises a processor 402, coupled to a memory 403. Furthermore, the system can include a display device 404 (e.g. for displaying patient images and dose distributions, a graphical user interface, and any other information related to treatment planning), a data input device 405 (e.g. a keyboard, a mouse or any other suitable device for data input) and a data reading/writing device 406 (e.g. an optical drive, USB interface, or any other suitable device for reading/writing data). The processor 402 can be of any kind, such as one or more central processing units (CPU) or any kind of parallel processor system, e.g. based on one or more graphics processing units (GPU). The memory 403 can be any kind of volatile or non-volatile memory suitable for storing and retrieving information, such as, for example, a hard drive. The memory 403 has a computer program 407 stored thereon. The computer program 407 comprises computer-readable instructions for performing the treatment planning method, where the computer-readable instructions can be transferred to, and executed by, the processor 402. When executed by the processor 402, the computer-readable instructions will perform a method as illustrated in FIG. 1 involving retrieving an initial treatment planning result comprising an initially planned dose and generating a treatment plan at least partly based on the initially planned dose. The generated treatment plan can be stored on the memory 403. The computer program 407 can also be stored on a non-transitory computer readable medium 408, e.g. a USB drive, an optical data carrier such as a CD-ROM, or any other suitable portable information storage device, so that the computer program 407 can be loaded to the memory 403 and/or transferred to different computing systems. The system described with reference to FIG. 4 is merely an example, and a computer system according to the invention does not necessarily comprise all the illustrated components, and/or might comprise other components not illustrated.

The invention has been described with reference to a number of example embodiments. It is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for generating a radiotherapy treatment plan for a patient, said method comprising, in a processor:
obtaining an initial radiotherapy treatment plan comprising an initial dose distribution;
modifying the initial dose distribution for at least one region of the patient to obtain a modified dose distribution; and
optimizing an objective function using the modified dose distribution as an optimization objective included in the objective function to generate the radiotherapy treatment plan, wherein the radiotherapy treatment plan is configured to deliver a radiation dose to the patient when the radiotherapy treatment plan is executed on a treatment machine.

2. The method according to claim 1, wherein said initial radiotherapy treatment plan comprises initially planned treatment parameters which are utilized as a starting point for generating the radiotherapy treatment plan.

3. The method according to claim 1, wherein a spatial dose distribution corresponding to said initial dose distribution is used as an additional optimization objective included in the objective function.

4. The method according to claim 1, wherein a dose volume histogram corresponding to said initial dose distribution is used as an additional optimization objective included in the objective function.

5. The method according to claim 1, wherein a characteristic dose fall-off corresponding to said initial dose distribution is used as an additional optimization objection included in the objective function.

6. The method according to claim 1, wherein an additional optimization objective included in the objective function is not based on said initial dose distribution.

7. The method according to claim 1, wherein a user interactively applies one or more modifications to the initial dose distribution while monitoring an optimized dose distribution being generated during the optimizing step until a satisfactory result corresponding to a current optimized dose distribution has been obtained.

8. The method according to claim 7, wherein the initial dose distribution is replaced with the current optimized dose distribution.

9. The method according to claim 1, wherein the optimizing of treatment parameters involves optimizing machine parameters.

10. The method according to claim 1, wherein user-input via a user-input interface defines an additional optimization objective included in the objective function.

11. The method according to claim 10, wherein the additional optimization objective included in the objective function is an additional modified dose distribution defined by a user-input modifying said initial dose distribution.

12. A computer program product comprising computer-readable instructions which, when executed on a computer, causes the computer to perform a method according to claim 1.

13. The computer program product according to claim 12, configured for receiving user-input defining an additional optimization objective included in the objective function.

14. The computer program product according to claim 13, wherein the additional optimization objective included in the objective function is an additional modified dose distribution defined by a user-input modifying said initial dose distribution.

15. A computer system comprising a processor coupled to at least one memory having stored thereon a computer program comprising computer-readable instructions, said processor configured to, by executing said computer-readable instructions, perform a method according to claim 1.

16. The computer system according to claim 15, wherein the system further comprises a data input device enabling a user to input data regarding an additional objective and/or a modification of said initial dose distribution.

* * * * *